United States Patent [19]

Hoy et al.

[11] Patent Number: 5,208,030
[45] Date of Patent: May 4, 1993

[54] ACTIVE INGREDIENT DOSAGE DEVICE

[75] Inventors: John Hoy, Rivonia; Phillipus J. van Rensburg, Randburg, both of South Africa

[73] Assignee: Imperial Chemical Industries PLC, London, Great Britain

[21] Appl. No.: 574,630

[22] Filed: Aug. 29, 1990

[30] Foreign Application Priority Data

Aug. 30, 1989 [ZA] South Africa .................. 89/6653

[51] Int. Cl.$^5$ .................. A01N 25/10; A01N 25/08; A01N 25/04
[52] U.S. Cl. .................. 424/409; 424/405; 424/408; 424/466; 514/772.5; 514/778.781
[58] Field of Search .............. 424/464, 465, 468, 469, 424/470, 484, 489, 405, 408, 466, 409; 514/772.5, 778, 781

[56] References Cited

U.S. PATENT DOCUMENTS

| | | | |
|---|---|---|---|
| 3,639,617 | 2/1972 | King | 424/300 |
| 3,657,446 | 4/1972 | Blackmore | 424/274 |
| 4,606,909 | 8/1986 | Bechgaard et al. | 424/21 |
| 4,677,003 | 6/1987 | Redlich et al. | 427/373 |
| 4,943,449 | 7/1990 | Aishima et al. | 427/213.3 |

FOREIGN PATENT DOCUMENTS

| | | |
|---|---|---|
| 0000260 | 1/1979 | European Pat. Off. . |
| 0127773 | 12/1984 | European Pat. Off. . |
| 8805890 | 4/1989 | South Africa ............ 424/405 |
| 2139893 | 11/1964 | United Kingdom . |
| 90/00007 | 1/1990 | World Int. Prop. O. . |

OTHER PUBLICATIONS

J. W. Conine et al., "Preparation of Solid Pharmaceutical Spheres" Apr. 1970, D+CI, pp. 38–41.
Alfonso R. Gennaro, "Remingtons Pharmaceutical Sciences". 1985, pp. 1615–1623.
Chiou W. L. et al., J. Pharm. Sci. 60(a) 1281–1302 (1971), entitled "Pharmaceutical Applications of Solid Dispersion Systems".

*Primary Examiner*—Thurman K. Page
*Assistant Examiner*—P. Kulkosky
*Attorney, Agent, or Firm*—William E. Dickheiser

[57] ABSTRACT

A method of making a dosage device comprises admixing at least one active ingredient which is in solid form at 25° C. and which has an average particle size of less than 5 microns, with a disintegrating agent, to provide a compressible mix; and compressing the mix into a unitary dosage device.

9 Claims, No Drawings

ACTIVE INGREDIENT DOSAGE DEVICE

This invention relates to a dosage device. It relates also to a method of forming a dosage device, and to a method of treating an article or locus.

According to a first aspect of the invention, there is provided a method of making a dosage device, which method comprises admixing at least one active ingredient which is in solid form at 25° C., and which has an average particle size of less than 5 microns, with a disintegrating agent, to provide a compressible mix; and compressing the mix into a unitary dosage device.

The method may include comminuting the active ingredient in solid form and having an average particle size greater than 5 microns, to have an average particle size of less than 5 microns. The active ingredient may be comminuted sufficiently to have an average particle size of 1-3 microns. In one embodiment of the invention, the comminution may be effected by dry milling the active ingredient, e.g. by means of micronization, to the desired particle size. The milled active ingredient may then be admixed with the disintegrating agent in particulate form. In another embodiment of the invention, the comminution may be effected by forming a suspension concentrate of the active ingredient in a suitable carrier liquid in which the active ingredient is non-soluble or sparingly soluble, and wet milling the suspension concentrate to obtain the desired active ingredient particle size. The suspension concentrate may then be admixed with the disintegrating agent by absorbing it into the disintegrating agent. The milled suspension concentrate may, however, be spray dried, if desired, and then admixed with the disintegrating agent.

While the active ingredient can be any suitable active ingredient, such as a therapeutic agent, anthelmintic, a pigment or dye, or the like, the Applicant believes that the method will find particular, but thus not necessarily exclusive, application in making dosage devices in which the active ingredient is a pesticide, e.g. an insecticide, herbicide, fungicide, or the like.

The pesticide may be one which is sparingly soluble in water, with water hence being the carrier liquid for use in forming the suspension concentrate and the concentration of the pesticide in the water, in the suspension concentrate, thus being greater than the solubility limit of the pesticide in water. The pesticide may have a water solubility of less than 1000 mg/l at 25° C., preferably less than 50 mg/l at 25° C. Preferably, the pesticide should have a melting point exceeding 70° C.

The pesticide may be a herbicide such as atrazine, simazine, cyanazine, terbuthylazine, diuron, chlorsulphuron, metsulfuron, tralkoxydin, or 2-(2-chloro-4-mesylbenzoyl) cyclohexane-1,3-dione; an insecticide such as deltamethrin, lindane, carbaryl, endosulfan, or carbofuran; a fungicide such as thiophanate methyl, carbendazim, flutriafol, hexaconazole, chlorothalonil, copper oxychloride, captan or thiram; or an acaricide such as hexythiazox, cyhexatin or amitraz.

The dosage device may comprise, on a mass basis active ingredient—5-60 parts self disintegrating agent—20-70 parts.

The disintegrating agent may be capable of disintegrating by effervescing or swelling on contact with water. When it is capable of swelling on contact with water, it may be a cross-linked polyvinyl pyrrolidone which also acts as a binder. For example, the cross-linked polyvinylpyrrolidone may then be that available under the trade name POLYPLASDONE XL from GAP Corp., or that available under the trade name KOLLIDON CL from BASF. However, it can instead be any other suitable disintegrating agent capable of swelling on contact with water such as a modified cellulose gum, for example that available under the trade name AC-DI-SOL from FMC Corporation, or a sodium starch glycolate such as that available under the trade name EXPLOTAB from Protea Chemical Services. When it is capable of effervescing on contact with water, it may be an acid and base combination such as tartaric acid and an alkali metal carbonate or bicarbonate, e.g. sodium bicarbonate.

The method may include admixing at least one further substance with the active ingredient, before comminution thereof and/or after comminution thereof. Thus, when the suspension concentrate is formed, the method may include adding at least one dispersing agent to the suspension concentrate before wet milling thereof. When dry milling is effected, the dispersing agent may be added before or after the milling. The dispersing agent may be a surfactant such as that conventionally used in a wettable powder or suspension concentrate formulation, for example sodium lignosulphonate; sodium naphthalene sulphonic acid/formaldehyde condensate; sodium alkyl aryl sulphonate; a nonyl phenol alkylene oxide, such as nonyl phenol ethylene oxide condensate or nonyl phenol ethylene/propylene oxide; a sodium lauryl sulphate which also acts as wetting agent, such as that available under the trade name EMPICOL LZ from Lankro; a sodium diisopropyl naphthalene sulfonate which also acts as wetting agent, such as that available under the trade name AEROSOL OS from Cyanamid; a sodium salt of naphthalene sulfonic acid formaldehyde condensate, such as that available under the trade name TAMOL NNO from BASF; oxyethylated polyarylphenol phosphate, which is a dispensing agent in aqueous media, and an example of which is obtainable under the trade name SOPROPHOR FL from Rhone-Poulenc; or the like.

The further substance may instead or also comprise one or more of the following:

an absorptive carrier such as a colloidal silica, for example AEROSIL 200 (trade name), diatomaceous earth, or a clay such as attapulgite;

a binder such as a microfine cellulose, for example that obtainable under the trade name ELCEMA P100 from Degussa, and which also acts as a filler and disintegrating agent; or lactose monohydrate, for example that obtainable under the trade name LUDIPRESS from BASF, and which is also a direct tabletting auxiliary;

a lubricant such as magnesium stearate;

a flow improving agent such as an absorptive silica, for example SIPERNAT 22S (trade name) from Degussa, which is a spray-dried ground silica, and acts as a free flow/anti-caking agent; and a water soluble filler such as soluble starch, urea, or sodium chloride.

The dosage device may comprise, by mass

| active ingredient | 5-60% |
| --- | --- |
| binder | 10-30% |
| flow improving agent | 0.5-10% |
| wetting/dispersing agent | 0.5-5% |
| disintegrating agent | 3-50% |
| lubricant | 0,05-2% |

-continued

| filler | 2-30% |

The invention also extends to a dosage device when made in accordance with the method of the first aspect of the invention.

According to a second aspect of the invention, there is provided a dosage device which is in compressed unitary form and which comprises an admixture of an active ingredient which is in solid form at 25° C. and which has an average particle size of less than 5 microns, and a disintegrating agent. According to a third aspect of the invention, there is provided a method of treating an article or locus, which comprises introducing a dosage device according to the invention, into a predetermined volume of water, with the volume of water being such that the concentration of the active ingredient in the water is greater than the solubility limit of the active ingredient in the water;

allowing the dosage device to disintegrate, thereby to form a suspension of the active ingredient in the water; and applying the suspension to an article or locus to be treated.

The invention will now be described by way of the following non-limiting examples (all proportions in parts by mass):

EXAMPLE 1

Step 1

A suspension concentrate having the following composition was made up by admixing the following components:

| | |
|---|---|
| as active ingredient, thiophanate methyl, technical (93% pure) (equivalent to 40,08 parts active ingredient) | 43.10 |
| as dispersing agent, TAMOL NNO | 3.50 |
| as further dispersing agent, TERIC 200 (trade name) which is a nonyl phenol alkylene oxide condensate available from ICI Austrialia | 1.50 |
| as antifoaming agent, SILCOLAPSE 5000A (trade name) which is an antifoaming silicone and is obtainable from ICI | 0.04 |
| water | 51.86 |

The suspension concentrate was milled by passing it twice through a horizontal bead mill (laboratory model KDL Dyno-mill) to obtain an average solids particle size of 2 microns.

Step 2

Tablets were formed having the following composition:

| | |
|---|---|
| suspension concentrate from Step 1 (equivalent to 35.0 parts active ingredient) | 87.32 |
| as wetting agent, EMPICOL LZ | 1.0 |
| as flow improving agent, SIPERNAT 22S | 0.5 |
| as disintegrating agent, POLYPLASDONE XL | 40.9 |
| as binder, ELCEMA P100 | 15.4 |
| as lubricant, magnesium stearate | 0.1 |

To form the tablets, the following steps were followed:

(i) The suspension concentrate was absorbed into the disintegrating agent;
(ii) This mixture was granulated by passing it through a 16 mesh British Standard Sieve;
(iii) The granules were then dried in a vacuum oven at 70° C.;
(iv) The remainder of the constituents were admixed with the dried granules; and
(v) The mixture was pressed into 2.5 g tablets at 1 tonne pressure.

Each tablet hence contained 0.875 gms active ingredient. In use, 1 tablet is added to 1 liter of water at ambient temperature, e.g. at 25° C. The tablet disintegrates within 30 seconds to form a suspension of the active ingredient in the water. Microscopic examination of the suspension revealed that most of the suspended particles were in the 1–3 micron range.

EXAMPLE 2

Step 1

A suspension concentrate having the composition as set out hereunder was made up and milled as described in EXAMPLE 1.

| | |
|---|---|
| hexaconazole, technical (87,3% pure) (equivalent to 20 parts active ingredient) | 22.9 |
| TERIC 200 | 2.6 |
| SILCOLAPSE 5000A | 0.1 |
| water | 74.4 |

Step 2

Tablets were made up to have the composition as set out hereunder, following the procedure of EXAMPLE 1 save that the dispersing agent was added to the milled suspension concentrate before it was absorbed into the disintegrating agent.

| | |
|---|---|
| suspension concentrate from Step 1 (equivalent to 30 parts active ingredient) | 150.0 |
| POLYPLASDONE XL (disintegrating agent) | 58.4 |
| SOPROPHOR FL (dispersing agent) | 3.1 |
| magnesium stearate | 0.1 |

When the resulting tablets were dispersed in standard hard water containing 340 ppm calcium as calcium carbonate, to a concentration of 0.005% active ingredient, a suspensibility of 88% after 30 minutes was obtained.

EXAMPLE 3

Step 1

A suspension concentrate having a composition as set out hereunder was made up and milled as described in EXAMPLE 1.

| | |
|---|---|
| deltamethrin, technical (98% pure) (equivalent to 64 parts active ingredient) | 65.31 |
| TERIC 200 | 2.73 |
| SILCOLAPSE 5000A | 0.08 |
| water | 31.47 |

Step 2

Tablets were made up to have the composition as set out hereunder, following the procedure of EXAMPLE 1, except that the mixture was not granulated but was pressed directly, after drying, using a commercial MANESTY press.

| | |
|---|---|
| suspension concentrate from Step 1 (equivalent to 40 parts active ingredient) | 62.50 |
| KOLLIDON CL (disintegrating agent) | 24.25 |
| ELCEMA P100 (binder) | 30.60 |
| EMPICOL LZ (wetter) | 2.0 |
| SIPERNAT 22 S (flow improving agent) | 0.50 |
| magnesium stearate | 0.10 |

The tablets were evaluated by dispersing them in water at the rate of 1 tablet of 2.5 gm (1 gm active ingredient) in 5 liters of water, i.e. 0.2 gm active ingredient per liter of water. The solubility of deltamethrin in water at 20° C. is less than 2 micrograms/liter of water. The tablets disintegrated within 30 seconds. Suspensibility tests indicated that 65% of the active ingredient was still in suspension after 30 minuts in standard hard water containing 340 ppm calcium as calcium carbonate.

EXAMPLE 4

Step 1

A suspension concentrate having a composition as set out hereunder was made up and milled as described in EXAMPLE 1:

| | |
|---|---|
| atrazine, technical (98% pure) | 50.0 |
| TERIC 200 | 2.5 |
| SILCOLAPSE 5000A | 0.1 |
| water | 47.4 |

Step 2

Tablets were made up to have the composition as set out hereunder, following the procedure set out in EXAMPLE 1:

| | |
|---|---|
| suspension concentrate from Step 1 (equivalent to 36.45 parts active ingredient) | 74.4 |
| KOLLIDON CL | 27.9 |
| ELCEMA P100 | 28.4 |
| EMPICOL LZ | 4.0 |
| SIPERNAT 22S | 0.5 |
| magnesium stearate | 0.1 |

20 mm diameter tablets weighing 3.5 gms each were pressed at 5 MPa, using a laboratory precision press. The resulting tablets were evaluated for hardness by subjecting single tablets to an increasing mass applied edge-on. The tablets withstood pressures up to 5 kg. Disintegration time was measured by dropping a single tablet into approximately 2 liters of water at ambient temperature, and agitating lightly. The test tablet disintegrated completely within 30 seconds. Microscopic examination of the resultant suspension revealed that most particles were in the 1-3 micron range.

EXAMPLE 5

2.5 gm tablets were made up by homogeneously admixing the components as set out hereunder, and pressing them into the tablets at 1.5 tonnes pressure.

| | |
|---|---|
| deltamethrin, technical | 40.0 |
| EMPICOL LZ (wetting agent) | 2.0 |
| TAMOL NNO (dispersing agent) | 5.0 |
| KOLLIDON CL (disintegrating agent) | 25.0 |
| ELCEMA P100 (binder) | 27.4 |
| SIPERNAT 22S (flow improving agent) | 0.5 |
| magnesium stearate (lubricant) | 0.1 |

The deltamethrin is dry milled prior to the admixing thereof to have an average particle size less than 5 microns. For example, it may be in micronized form as available from Roussel Uclaf, with 50% (by mass) of its particles having a particle size less than 2 microns. Alternatively, the suspension concentrate of Example 3 can be spray dried, and the resultant powder admixed with the remaining ingredients as set out above.

The tablets, when introduced into water at the rate of one tablet in 5 liters of water, disintegrate within 1 minute. Microscopic examination revealed that most of the particles in the suspension were in the 2 micron range. The Applicant has found that with active pesticides requiring a very low rate of application, typically in the order of a few grams per hectare, very small pesticide particles, typically having an average particle size less than 5 microns, dispersed in the prescribed carrier liquid, usually water, are highly desirable for effective, accurate and even distribution of the pesticide on application. Furthermore, the smaller the particle size, the greater the surface area thereof, which promotes effective release of the pesticide after application to a locus or substrate. However, it has hitherto been a problem when providing pesticides in tablet form, that if the pesticide particles are too small, unsatisfactory dispersion rates of the tablet in the carrier liquid result. However, it has surprisingly been found that in the method and dosage device of the present invention in which the average pesticide particle size is less than 5 microns, and typically in the order of 1 to 3 microns, rapid disintegration and dispersion rates are achieved. Moreover, the resulting tablets have adequate hardness which permit handling in the field, and the tablets on dispersion have excellent suspension properties.

The dosage devices of the present invention thus provide a good vehicle for such pesticides, since they are compact and hence easily transported and stored, and are also in a form in which they are handled safely. Furthermore, there is not a problem of having to dispose of large used pesticide containers. They are furthermore easy to disperse and apply effectively and accurately as set out hereinbefore, i.e. with little wastage. Furthermore, the Applicant was also surprised to find that the resulting average pesticide particle size of the active ingredient, after the tablets had been dispersed in water, was of the desired order of 1-3 microns in spite of the fact that the active ingredient, after having been milled down to less than 5 microns, was then compressed with the disintegrating agent into tablet form during which agglomeration into larger particle sizes would have been expected. However, as stated, it was surprisingly found that the average particle size of the active ingredient, in the resultant suspensions, was still in the range of 1-3 microns.

We claim:

1. A dosage device which is in compressed unitary form and which comprises an admixture of a pesticide which is in solid form at 25° C., is sparingly soluble in water, and has an average particle size of 1 to 3 microns, and a disintegrating agent, with the device being capable of disintegrating in water to form a suspension of the pesticide in the water, when introduced into sufficient water such that the concentration of the pesticide in the water is above the solubility limit of the pesticide in water, with the average particle size of the pesticide in the suspension being in the range of 1 to 3 microns.

2. A dosage device which is in compressed unitary form and which comprises an admixture of a pesticide which is in solid form at 25° C., is sparingly soluble in water, and has an average particle size of less than 5 microns, and a disintegrating agent, with the device being capable of disintegrating in water to form a suspension of the pesticide in the water, when introduced into sufficient water such that the concentration of the pesticide in the water is above the solubility limit of the pesticide in water.

3. A dosage device according to claim 2, wherein the pesticide has a water solubility of less than 1000 mg/l at 25° C., and the average particle size of the active ingredient is from 1 to 3 microns.

4. A dosage device according to claim 3, wherein the pesticide is selected from the group consisting in an insecticide, herbicide, fungicide and an acaricide, with the disintegrating agent being capable of disintegrating the device by effervescing or swelling on contact with water.

5. A dosage device according to claim 4, wherein the pesticide is selected from the group consisting in atrazine, simazine, cyanazine, terbuthylazine, diuron, chlorsulphuron, metsulfuron, tralkoxydim, 2-(2-chloro-4-mesylbenzoyl) cyclohexane1,3-dione, deltamethrin, lindane, carbaryl, endosulfan, carbofuran, thiophanate methyl, carbendazim, flutriafol, hexaconazole, chlorothalonil, copper oxychloride, captan, thiram, hexythiazox, cyhexatin and amitraz, with the disintegrating agent being selected from the group consisting in a cross-linked polyvinyl pyrrolidone, a modified cellulose gum, a sodium starch glycolate, and an acid/base combination.

6. A dosage device according to claim 2 which is that obtained by forming a suspension concentrate of the pesticide in a suitable carrier liquid in which the pesticide is nonsoluble or sparingly soluble, wet milling the suspension concentrate to obtain the pesticide average particle size of less than 5 microns, admixing the suspension concentrate with the disintegrating agent by absorbing it into the disintegrating agent, and compressing the resultant mix into the unitary form.

7. A dosage device comprises:
   5-60% by mass of a pesticide selected from the group consisting of atrazine, simazine, cyanazine, terbuthylazine, diuron, chlorsulfuron phuron, metsulfuron, tralkoxydim, 2-(2-chloro-4-mesylbenzoyl) cyclohexane-1,3-dione, deltamethrin, lindane, carbaryl, endosulfan, carbofuran, thiophanate methyl, carbendazim, flutriafol, hexaconazole, chlorothalonil, copper oxychloride, captan, thiram, hexythiazox, cyhexatin, amitraz and combinations thereof;
   3-50% by mass of a disintegrating agent selected from the group of cross-linked polyvinyl pyrrolidone, a modified cellulose gum, a sodium starch glycolate, an acid/base combination and combinations thereof;
   10-30% by mass of a binder selected from the group consisting of a microfined cellulose, lactose monohydrate and combinations thereof;
   0.5%-10% by mass of a flow improving agent;
   0.5-5% by mass of a wetting/dispersing agent selected from the group consisting of sodium lignosulphonate, sodium naphthalene sulphonic acid/formaldehyde condensate, sodium alkyl aryl sulphonate, a nonyl phenol alkylene oxide, a sodium lauryl sulphate, a sodium diisopropyl naphthalene sulfonate, a sodium salt of naphthalene sulfonic acid formaldehyde condensate, oxyethylated polyarylphenol phosphate and combinations thereof;
   0.5-2% by mass of a lubricant;
   2-30% by mass of a filler selected from the group consisting of soluble starch, urea, sodium chloride and combinations thereof.

8. A method of treating an article or locus, which comprises
   introducing a dosage device as claimed in any one of claims 2 to 7 inclusive, into a predetermined volume of water, with the volume of water being such that the concentration of the active ingredient in the water is greater than the solubility limit of the active ingredient in the water;
   allowing the dosage device to disintegrate, thereby to form a suspension of the active ingredient in the water; and
   applying the suspension to an article or locus to be treated.

9. A method of treating an article or locus, which comprises
   introducing a dosage device as claimed in claim 1, into a predetermined volume of water, with the volume of water being such that the concentration of the active ingredient in the water is greater than the solubility limit of the active ingredient in the water;
   allowing the dosage device to disintegrate, thereby to form a suspension of the active ingredient in the water; and
   applying the suspension to an article or locus to be treated.

* * * * *

UNITED STATES PATENT AND TRADEMARK OFFICE
CERTIFICATE OF CORRECTION

PATENT NO. : 5,208,030
DATED : May 4, 1993
INVENTOR(S) : John Hoy and Phillipus J. van Rensburg It is certified that error appears in the above-identified patent and that said Letters Patent is hereby corrected as shown below:

On the title page

[73] Assignee: "IMPERIAL CHEMICAL INDUSTRIES PLC London, Great Britain" should read -- [73] Assignee: AECI LIMITED
16th Floor, Office Tower
Carlton Centre
Commissioner Street
Johannesburg, Transvaal
South Africa --

Signed and Sealed this

Sixth Day of June, 1995

Attest:

BRUCE LEHMAN

Attesting Officer

Commissioner of Patents and Trademarks